United States Patent
Siudzinski

[19]

[11] Patent Number: 5,772,649
[45] Date of Patent: Jun. 30, 1998

[54] PANEL ATTACHMENT FOR ABSORBENT UNDERGARMENTS

[76] Inventor: Betty S. Siudzinski, 10 408 Broadfield Ct., Potomac, Md. 20854

[21] Appl. No.: 705,730

[22] Filed: Aug. 30, 1996

Related U.S. Application Data

[63] Continuation-in-part of Ser. No. 395,109, Feb. 27, 1995, abandoned.

[51] Int. Cl.$^6$ ................................................ A61F 13/15
[52] U.S. Cl. ........................ 604/386; 604/391; 604/393
[58] Field of Search ................................. 604/386, 389, 604/391, 393, 385.1, 392, 400

[56] References Cited

U.S. PATENT DOCUMENTS

| 4,728,326 | 3/1988 | Gilles | 604/391 |
| 5,106,385 | 4/1992 | Allen | 604/391 |
| 5,261,901 | 11/1993 | Guay | 604/391 |
| 5,445,628 | 8/1995 | Gipson | 604/392 |

FOREIGN PATENT DOCUMENTS

| 68065 | 3/1958 | France | 604/386 |
| 476600 | 12/1937 | United Kingdom | 604/386 |

Primary Examiner—Michael J. Milano
Attorney, Agent, or Firm—Robert Halper

[57] ABSTRACT

A panel attachment that extends the size of diapers, other absorbent undergarments or non-absorbent garments to be worn by growing infants. The panel attachment can be attached to a disposable or reusable diaper, detached when the diaper is soiled and reattached to a replacement diaper. The panel attachment can also be attached to a diaper cover or similar garment to extend its use for growing infants. The panel attachment comprises a sheet or sheets of material corresponding to the specific sizes of diapers or other similar garments on the market with a plurality of fasteners such as adhesive tabs hook and loop material and snap fasteners, corresponding to the fasteners of the diapers or other garments. The panel attachment can be made adjustable in size by extending the width of the panel or increasing its length. The panel also has indicia to indicate where to attach the diaper to the panel to achieve a specific increment in length. The panel's aesthetic appearance can be improved by attaching a fringe of lace thereto as well as making the panel in a variety of colors. By shaping the panel in a defined geometry, considerable saving of material can be achieved.

11 Claims, 2 Drawing Sheets

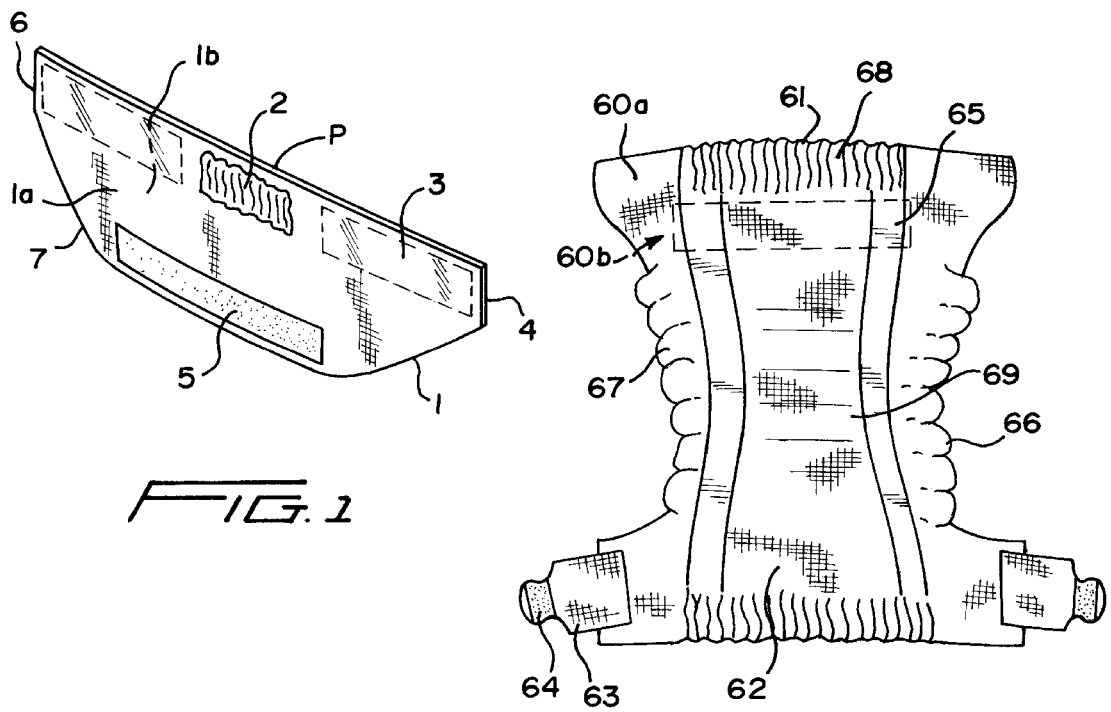
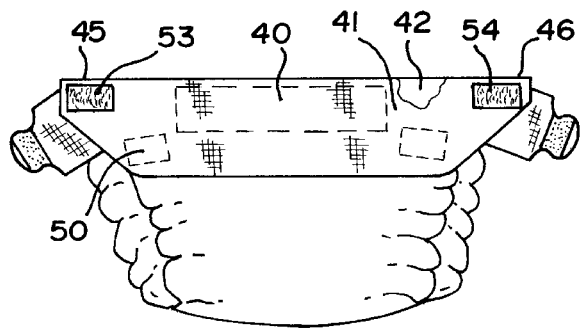
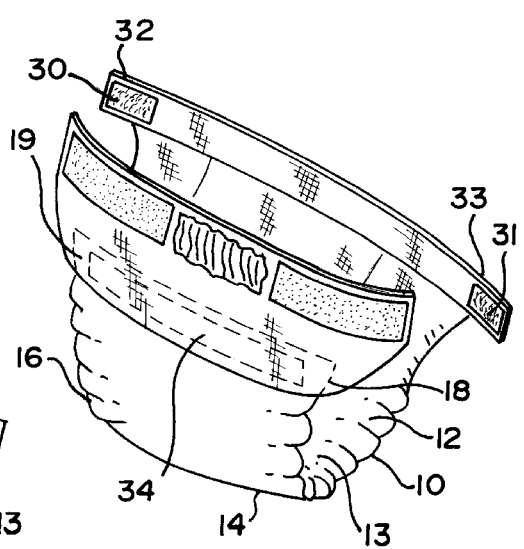

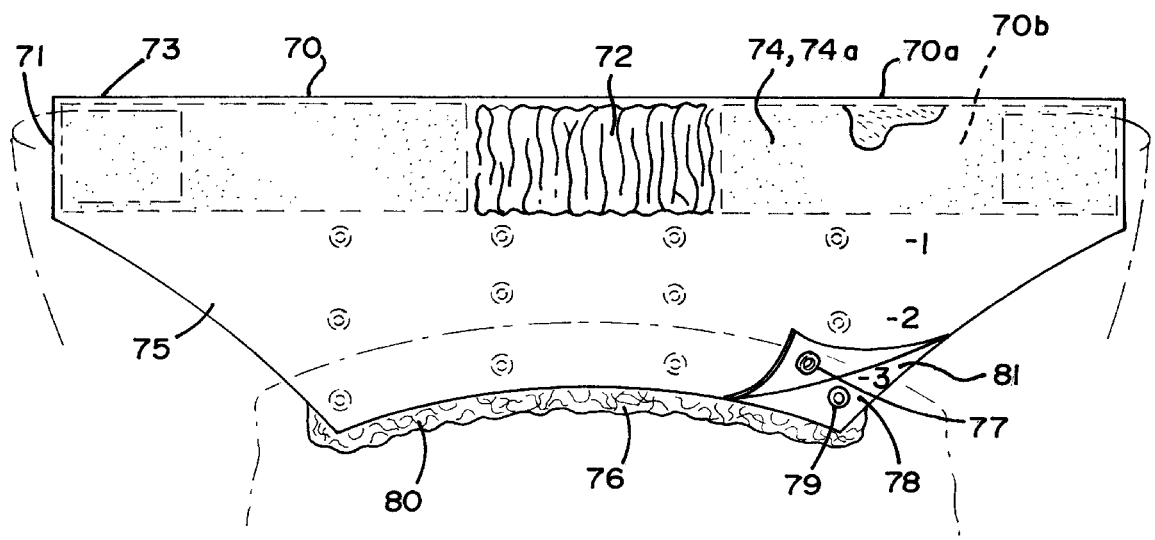
FIG. 6
FIG. 7
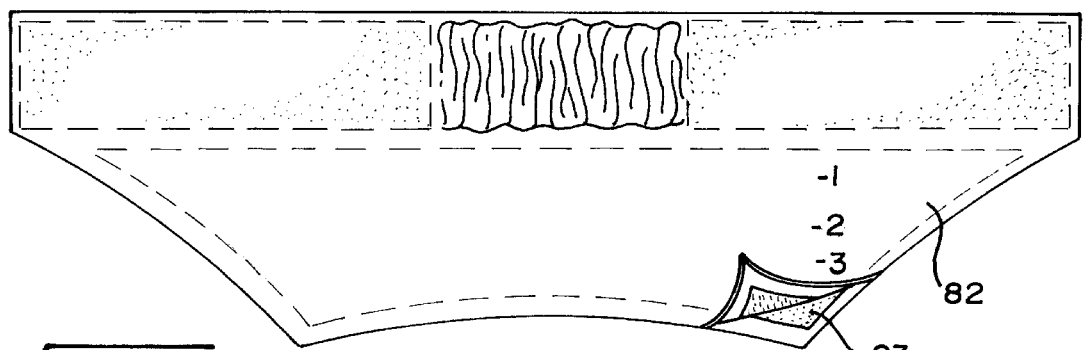
FIG. 8
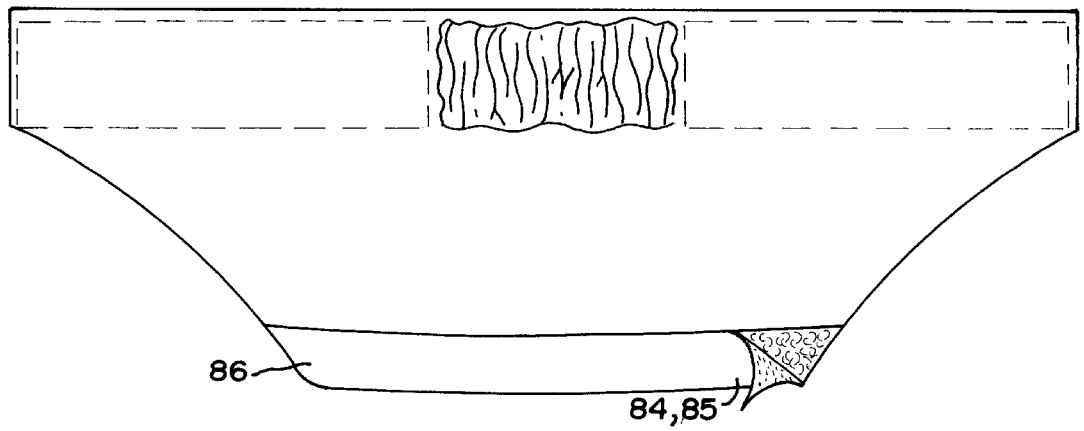

PANEL ATTACHMENT FOR ABSORBENT UNDERGARMENTS

This application is a continuation in part of application Ser. No. 08/1395109, filed on Feb. 27, 1995, now abandoned.

FIELD OF INVENTION

This invention relates to a panel attachment for holding together, varying the size, and extending the utility of a plurality of objects, specifically baby diapers, incontinence articles and other absorbent undergarments.

BACKGROUND OF THE INVENTION

Diapers currently produced and sold on the market by various manufacturers are generally designed to fit babies in various stages of growth from newborn to toddler. Manufacturers construct diapers to fit specific ranges of body sizes based on weight. As babies grow in size and weight, they outgrow one type of diaper designed for a specific range, necessitating a switch to th next size range for diapers. For example, a baby at birth is on average about 20" in height and over a period of three years, the projected period of usage, the baby can be expected to grow to about 38". Diapers sold at most stores today come in 5 sizes, (1), small for a baby up to 14 pounds, (2) small to medium from 12 to 14 pounds, (3), medium 16–28 pounds, (4), large 22–37 pounds and (5) extra large over 30 pounds. When babies outgrow one size range of diapers, parents are forced to purchase the next larger size range which often come in packages of lower quantity and higher price than packages containing the smaller size range of diapers. From an economic and environmental viewpoint this practice is unsound. Use of larger sized disposable diapers entails unnecessary waste of material. In a day and age when landfills are overflowing with non-degradable disposable diapers, any reduction in disposal of materials is invaluable.

Some attempts at reducing the need for a multitude of differently sized diapers have resulted in several versions of adjustable or variable sized reusable diapers; however, the majority of prior art patents consist of a single, integral diaper and/or a diaper wrap that may be adjusted in size to fit any baby weighing from about 6 pounds to 30 pounds and over. One patent that makes use of a panel attachment is of limited use because it is designed with a specific type diaper in mind. Furthermore, a number of the adjustable diapers are also of the reusable type. Adjustable reusable diapers necessitate continuous cleaning of either the whole diaper, or a component thereof such as an inner absorbent panel. Inner absorbent panels require parents to remove the entire diaper from a baby, separate the inner absorbent panel, and replace it with a new absorbent panel. This process is cumbersome and inconvenient, especially where parents have taken their babies outside the house. Additionally inner absorbent panels tend to leak more often than disposable diapers. Thus the continued popularity of disposable diapers which reflects the scarcity of time available to most parents. Many parents also prefer not to be concerned with the care and laundering of diapers Specific examples of the prior art are U.S. Pat. No. 4,728,326 which is an example of an adjustable diaper that uses a pair of straps that extends through slotted opening in the body portion of the diaper to adjust its size. The strap is fastened to the diaper with hook and loop fasteners and and there are two sets of vertically spaced slots so that by folding the diaper and passing the strap through the lower set of openings the diaper can be made smaller U.S. Pat. No. 5,261,901 is an example of an adjustable and reusable diaper. The diaper consists of an inner pad and an outer panel The pad is not attached to the outer panel and is removable and washable separately. The outer panel has a front flap with a waistband and a rear flap with a wider waistband. The outer face of the waistband on the front flap has a loop fabric strip, There are also fastening strips on the outer faces of the end sections of the rear flaps. Another fastening strip is also secured to the inner faces of the rear flap at corresponding positions on the outer side. Thus the strap from the rear flap can be attached to the front flap at a variety of positions depending on the age and size of the infant. U.S. Pat. No. 5,445,628 shows a disposable diaper assembly which can be attached to a belt that is reusable. The belt has indicia so that the longitudinal center line of the belt can be matched to the longitudinal center line of the diaper assembly. The belt has a hook type material along its entire length so that the belt can be adjustably attached to the assembly at any number of positions as determined by the child size. U.S. Pat. No. 5,106,385 is another type of adjustable diaper involving a different principle. The diaper is made smaller or larger. In one embodiment the diaper is folded over to reduce the effective size This is accomplished by folding the top end of the diaper downwardly. In the second embodiment the diaper the diaper is not only reduced in length but also in the size of the waist. In this situation what is referred to as the wings of the diaper are folded laterally rearwardly and then downwardly. In another embodiment the length of the diaper is increased by the addition of an extension panel has an inner and lower set of fastening means for attachment to the upper edge of the diaper and another an upper and outer set of fasteners at the outer end of the extension panel to fasten to the diaper when the opposite end of the diaper is folded over. A British patent 476,600 shows an attachment to a diaper in the form of two bands that are secured by snap fasteners and have pockets to receive a replaceable and disposable diaper pad. The bands are not adjustable and have no effect on the size of the diaper either lengthwise or widthwise.

As can be seen from above, the diapers of the prior art for the most part while extending the girth of the diaper make no provisions for extending the length. The one diaper U.S. Pat. No. 5,106,385, that does make a provision for extending the length of the diaper is limited to the use of the particular design of diaper illustrated therein. Furthermore, while the diaper per se can be reduced in size, there is only one place of attachment of the panel to the diaper so that the overall length of diaper and panel cannot be varied. It is also not usable with the average or conventional diapers presently on the market without modification of the points of attachment.

It is accordingly an object of this invention to use an extension panel that is adaptable to any and all diapers that are presently on the market.

It is further an object of this invention to work with the smallest available disposable diapers and extend the size of such diapers to fit babies of larger size.

It is also an object of this invention to produce an extended diaper that conforms to the consumers'preference for the convenience of disposable diapers, yet satisfies their desire to reduce waste.

It is still an object of this invention to provide an efficient and time-saving product to the extent with which the ease of checking the diaper for soiling is made possible.

Other objects of the invention will become apparent from the description that follows

SUMMARY OF THE INVENTION

The present invention comprises a panel composed of a sheet or sheets of stitched material containing a plurality of fastening means so as to attach to a variety of diapers currently available in the market The material can be made of cloth or other non-disposable fabrics, that are the or liquid impermeable fabrics same or similar to the fabric generally utilized as the outer layer of disposable panels currently on the market. It is important to note that whatever material is used as the outer fabric of the panel, the inner fabric needs to feel comfortable and non-abrasive to babies' sensitive skin.

The fastening means of the panel should correlate to that of the desired diaper. Diapers currently on the market use a variety of fasteners such as snap fasteners, adhesive strips, and hook and loop fasteners including but not limited to the fastener known by the trademark VELCRO. The present invention is intended for use with small sized diapers already containing fasteners so that the size of such diapers can be extended to babies that have outgrown the smaller size. The panel can also be manufactured as a component of a separate and novel line of diapers. Accordingly, manufacturers of this invention can vary the fastening means if necessary to correspond with a wide variety of diapers or other absorbent undergarments, as well as diaper overwraps, diaper covers or other similar garments.

A first embodiment of the invention comprises a sheet of material containing three strips of material for fastening, with one strip comprising adhesive material and the other two strips comprising non-adhesive plastic material conducive to bonding with adhesive material. The sheet is liquid impermeable on both front and rear sides. The two strips of non-adhesive material are attached to the top sides of the rear face of the panel, The long strip of adhesive is attached to the bottom of the front face.

This panel of the invention can be adapted to a small sized diaper intended for a newborn so that the combined diaper and panel can then fit a baby that has just outgrown the newborn sized diaper. The diaper short strips can be made of non adhesive material with a long center strip made of adhesive plastic material. The two short strips are attached to each end flap extending horizontally from the top of the rear face of the diaper when folded. The long strip is horizontally attached to the top of the front face of the diaper. Ordinary use of the diaper would entail connecting each of the two short strips of adhesive material at the rear face of the diaper to opposite sides of the short strips of non-adhesive plastic on the rear face of the diaper. Another embodiment of the invention comprises a more flexible panel attachment wherein the panel has two flaps of material one foldable over the other wherein each flap comprises one or several rows of spaced fastening components and one edge of the unfolded diaper is fitted and secured between the flaps in the proper row according to the extent that the size of the diaper is to be increased. Indicia will mark off the placement of the diaper with respect to the row of fasteners desired. Above the flaps and integral therewith is a rectangular section having affixed to its outer face two strips of fastening material extending from the respective ends of the rectangular section and being either hook and loop complementary material or non-adhesive plastic conducive to fastening with an adhesive tape. Additionally a strip of hook or loop material could be arranged on the respective flaps, its length determined by the degree of adjustability of diaper desired.

BRIEF DESCRIPTION OF THE DRAWINGS

FIG. 1 is a front view of the panel of this invention.

FIG. 2 is an example of a typical commercial disposble diaper

FIG. 3 is an example of the extension panel of U.S. Pat. No. 5,106,385 and its lack of congruence with a standard diaper as shown in FIG. 2.

FIG. 4 is an example of the Allen diaper of U.S. Pat. No. 5,106,385 in unfolded position.

FIG. 5 is an example of the diaper of U.S. Pat. No. 5,106,385 in combination with the extension panel of the invention.

FIG. 6 is an example of another embodiment of the invention.

FIG. 7 is an example of the embodiment of FIG. 5 showing another type of fastener.

FIG. 8 is an example of an embodiment with the shape of FIG. I and the fastener of FIG. 7.

DETAILED DESCRIPTION OF THE INVENTION

FIG. 1 shows a front view of one embodiment of the panel attachment. The panel attachment P consists of a sheet 1 of non-absorbent stitched material having a front face 1a and a rear face 1b. In the middle of the top between the two faces is an elastic component 2 which is intended to facilitate adjustability of the panel to fit various size waists. More than a single elastic integrated component can be used. The panel attachment also has two short strips of non-adhesive plastic material 3 attached near the top edges of the rear face and extending inwardly from the end flaps 4. A long, flat strip of adhesive plastic material 5 is attached to near the bottom edge of the front face in the intermediate region of the panel. The panel has a first substantially rectangular segment.6 with an arcuate segment 7 devolving downwardly from the end flaps. The panel is made so that the width of the rectangular segment from end flap to end flap is greater than the width of the upper section of the diaper, but the width of the lower section of the diaper including the fastening tabs in extended position is wider than the width of the rectangular segment of the panel. Alternatively non-adhesive plastic material 3 could be attached to the front face and strip 5 could be attached to the rear face in the same corresponding locations.

FIG. 2 shows an example of the front face 60a of a typical diaper in unfolded position. The diaper has an upper section 61 and an lower section 62. On the front face of the lower section at each end is affixed a tab 63 containing a layer of adhesive 64. On the rear face 60b of the upper section and running across the top is a strip 65 of non-adhesive plastic material. Between the upper section and the lower section are a pair of concave edges 66 and stitched between the front and rear faces at these edges are a pair of elastic components 67. Elastic components 68 are also embedded into the waist area in the respective upper and lower sections midway between the ends. These elastic components ensure snug fits and prevent leakage of bodily waste. In the region of the concave edges and therebetween is an non-absorbent pad 69. It should be realized that a number of diapers also use other types of fasteners such as hook and loop material and snap fasteners.

FIG. 3 shows the extension panel of U.S. Pat. No. 5,106,385 and a typical diaper as shown in FIG. 2 and described above. Using the reference characters shown in FIGS. 3A–3D of that patent, 40 is the extension panel, which is folded over to have an inner layer 41 and an outer layer 42 having extension wing portions 45, 46 and fastener tabs 53, 54 on the inner surface of each wing. A pair of fastener tabs 50 are provided on the interior surface of the inner layer 41. These fastener tabs are hook and loop material. When a diaper of the kind just described above in FIG. 2, is slipped between the inner and outer layers of the extension panel 40 of FIG. 3, there is no mode of attachment since this folded over diaper has only a long strip of nonadhesive material which can not bind to the hook and loop material of FIG. 3. Similarly the hook and loop tabs on the wing portions of the panel are not able to fasten to the tapes with adhesive on the inner face of the diaper; moreover, assuming that this typical diaper also had hook and loop fasteners, the tabs 13 of that diaper when folded over would be exterior to the hook and loop material on the inner layer 41 of panel 40.

FIG. 4 shows the diaper of U.S. Pat. No. 5,106,385 in unfolded condition.

FIG. 5 shows the same diaper of FIG. 4 fastened to the extension panel of this invention. Using the reference characters of that patent as shown in FIGS. 1A–1D, Diaper 10 in unfolded condition comprises an elongate panel 12 having an inner surface 13 and an outer surface 14. The panel diverges away from center 16 into wing portions 18 and 19, each wing on opposite ends 20, 21. A first pair of fastener tabs 30,31 are laterally spaced from each other at end 20 on the inner surface of wings 18. A second pair of fastener tabs 32, 33 are disposed on the outer surface in back to back relationship with tabs 30, 31. A complementary fastener in the form of an elongate bar 34 is disposed on the outer surface at the opposite end 21 so as to extend intermediate the wing portions 19. If this diaper be folded as shown in FIG. 5, the bar 34 will mesh with the long strip 5 near the bottom surface of the arcuate segment 7 of the attachment panel and the fastener tabs 30, 31 will fold around the fastener material strips 3 of the rectangular section of the attachment panel, which as indicated above also may be of the hook and loop type.

FIG. 6 shows another extension panel 70 of the invention that comprises stitched sheets 70a, an inner face and 70b, an outer face of a washable cloth or liquid impermeable material. It is contemplated that this panel can be attached to a small size diaper and adjustably increase the size to accommodate a baby as it grows to an infant; however if so desired the panel could readily be attached to a larger size diaper. The panel is made in several segments. 71 is a substantially rectangular segment containing an elastic component 72 stitched within the sheets and located midway of the end flaps 73. Adjacent the elastic component and on each side thereof but on the outer face are strips of non-adhesive plastic 74 or hook and loop material 74a. These strips extend from adjacent the elastic to near the ends of the rectangular segment and are stitched on the outer face Extending downwardly from the rectangular segment are two arcuate segments 75 traversing a path from the ends of the rectangular segment to intersect a semicircular intermediate structure 76. Spaced along intermediate structure 76 are a plurality of the female complements 77 of snap fasteners. These complements are arranged in three rows of about four to a row with the complements being spaced and arranged to follow the outline of the semicircle The distance from the top edge of the panel to the point of intersection of the arc and the semicircle is about 6 inches. The length of the rectangular element is about two inches and the length of the intermediate structure is about four inches. The two end complements would be placed vertically about ½ inches above the point of intersection. The successive rows of complements would be spaced vertically about 1 and ⅜ inches apart. The successive rows, would be aligned with the complements of the first row. Underlying intermediate structure 76 and integral and coincident therewith, is another intermediate structure 78 identical to structure 76 except for the fact that this segment contains three rows of male complements 79 of snap fasteners which are arranged so as to be in corresponding spaced positions to engage the female complements. To improve the aesthetic appearance of the panel a fringe of lace 80 can be stitched to the bottom of the structures 76 and 78. Additionally, the panel can be made in a variety of colors, such as pink, blue, green, etc. The determination of the length of the panel is based on the difference in length of the smallest diaper and the extra large diaper which is about five inches. To achieve this increment, the top edge of the diaper is placed about ½ inch above the lowest row of snap fasteners To achieve an increment of about four inches the diaper need be raised only about an ⅛ inch above the next row of snap fasteners. On the panel will be placed indicia 81 in the form of small black lines with a corresponding dimension, for example three inches, showing where the diaper should be positioned on the panel to achieve that increment in length. As shown in FIG. 6, instead of using snap fasteners, segments 76 and 78 could have strips 82, 83 of hook and loop material shaped to the contour of the intermediate structures. In this case the indicia would be appropriately placed on the arcuate structures. Thus whatever the nature of the hook and loop material on the diaper it would still be able to fasten to at least one of the intermediate structures. If the panel needs to be washed, the intermediate structures containing the hook and loop material would be fastened together so as not to entangle any other garment being washed. The width of the upper section of the diaper when fully extended is about 9 inches and the width of the lower section of the diaper including the tab fasteners when fully extended is about fifteen inches. Therefore the width of the rectangular segment of the panel when fully extended should be less than the lower section of the diaper, about 12 inches. FIG. 8 is a modification of the panel having the shape of FIG. 1 and the fastener element of FIG. 7, except that the fastener length is much narrower. The central section of the arcuate segment 84 has a fold that enables it to be bent backward over a corresponding segment 85, wherein both segments are covered with a strip of hook or loop material 86. in fastening the upper section of a diaper to the panel, the diaper is placed on arcuate segment 84 and folded back so as to be secured between the two arcuate segments 84, 85.

The preferred shape of the panel is represented in the embodiments of FIGS 6 and 7. It is estimated that by using intermediate semicircular segments as much as 6 to 8 square inches of material per diaper can be saved. This amount accrues to a considerable saving considering that the panel will be made in large quantities.

While the invention has been described with specific embodiments it should be obvious to one skilled in the art that other variations and modifications could be made without departure from the scope of the appended claims.

I claim:

1. A modified diaper having a panel attachment to increase the size of the diaper comprising:

a) a diaper having an upper section and a lower section, an inner face and an outer face, laterally spaced end flaps, an absorbent pad within said faces, a pair of laterally spaced concave edges having elastic webbing thereat between said upper and lower sections, a pair of laterally spaced adhesive bearing fastening tabs at said lower section affixed to said inner face, and a strip of non-adhesive plastic extending midway of said end flaps across said outer face of said upper section, b) said panel attachment comprising a sheet of non-adsorbent material having a substantially rectangular upper segment with straight ends having an inner face and an outer face, an arcuate segment devolving downwardly and inwardly from said straight ends, an elastic webbing stitched between said inner and outer face of said rectangular segment and midway of said ends, a rectangular strip of adhesive plastic material on said inner face of said sheet and adjacent a lower edge of said arcuate segment, strips of non-adhesive plastic material on said outer face of said rectangular segment extending inwardly from said straight ends, c) said strip of non-adhesive plastic on said outer face of said diaper at the upper section being joined with said adhesive plastic strip on said inner face of said arcuate segment, and said diaper when folded being joined by said tabs on said diaper which extend around and over said non-adhesive plastic strips on said outer face of said panel.

2. The modified diaper of claim 1 wherein said rectangular segment of said panel is wider than said ends flap of said diaper upper section, but less than the width of said lower section including said fastening tabs attached thereto.

3. The modified diaper of claim 1 wherein said diaper is of the disposable type.

4. The modified diaper of claim 1 wherein said diaper is a non-disposable absorbent fabric such as cloth.

5. The modified diaper of claim 1 wherein said diaper is a small size diaper.

6. A modified diaper having a panel attachment to increase the size of the diaper, said diaper being secured to said panel by complementary hook and loop material comprising;

a) a diaper having an upper section and a lower section, an inner face and an outer face, laterally spaced end flaps, an absorbent pad within said faces, a pair of laterally spaced concave edges having elastic webbing thereat between said upper and lower sections, a pair of laterally spaced hook bearing material fastening tabs at said lower section, affixed to said inner face, and a strip of loop material extending midway of said flaps across said outer face of said upper section, b) said panel attachment comprising a sheet of non-absorbent material having a substantially rectangular upper segment with straight ends having an inner face and an outer face, an arcuate segment devolving downwardly and inwardly from said straight ends, an elastic webbing stitched between said inner and outer face of said rectangular segment and midway of said ends, a rectangular strip of hook material on said inner face of said sheet and adjacent a lower edge of said arcuate segment, strips of loop material on said outer face of said rectangular segment extending inwardly from said straight ends, c) said strip of loop material on said face of said diaper at the upper section being joined with said hook material on said inner face of said arcuate segment, and said diaper when folded being joined by said tabs on said diaper which extend around and over said loop material on said outer face of said panel.

7. The modified diaper of claim 6 wherein said arcuate segment has a central region with a fold spaced above a bottom edge of said arcuate segment, a corresponding arcuate segment above said fold, and said strip of loop material on said upper section of said diaper and said rectangular strip of hook material on said inner face of said arcuate segment has been replaced by a single strip of complementary hook and loop material on each of said segments such that when said upper section of said diaper is placed on said arcuate segment, said arcuate segment is folded back over said corresponding arcuate segment to secure said upper section of said diaper.

8. A modified diaper having a panel attachment to increase the size of the diaper comprising:

a) a diaper having an upper section and a lower section, an inner face and an outer face, laterally spaced end flaps, an absorbent pad within said faces, a pair of laterally spaced concave edges having elastic webbing thereat between said upper and lower sections, a pair of laterally spaced adhesive bearing fastening tabs at said lower section, affixed to said inner face, and a strip of non-adhesive plastic extending midway of said end flaps across said outer face of said upper section, b) said panel attachment comprising a sheet of non-absorbent material having a substantially rectangular upper segment with straight ends having an inner face and an outer face, an arcuate segment devolving downwardly and inwardly from said straight ends, an elastic webbing stitched between said inner and outer face of said rectangular segment and midway of said ends, said arcuate segment intersecting a semicircular intermediate structure folded over a corresponding and coincident semicircular intermediate structure having a plurality of rows of equally spaced female complements of snap fasteners arranged to follow the contour of said corresponding semicircular structure, said female complements being located above an arc formed by said semicircular structure with the female complements at ends of the arc being above the point of intersection of said arcuate segment and said corresponding semicircular intermediate structure having corresponding rows of equally spaced male complements of snap fasteners oriented so as to engage said female complements when said semicircular intermediate structure is folded over said corresponding intermediate structure, c) said upper section of said diaper being adjustably fastened to said panel by placing said upper section slightly above a selected row of said female complements of said snap fasteners and folding said semicircular intermediate structure over said corresponding intermediate structure and securing a corresponding selected row of said male complements of said snap fasteners to said female complements, d) said lower section of said diaper when folded being secured to said panel by placing said adhesive tabs around and over said non-adhesive plastic strips on the outer face of said rectangular segment.

9. The modified diaper of claim 8 wherein said panel attachment is enlarged by increasing the radius of curvature of said intermediate semicircular structures such that a plurality of spaced rows of snap fasteners are arranged on said intermediate semicircular intermediate structures wherein successive rows of snap fasteners are aligned to follow the contour of said semicircular intermediate structures, said complements at said ends above a first row being placed substantially vertical to said first row of fasteners and indicia including a dimension being appropriately placed on said corresponding intermediate semicircular structure to indicate the increment of length added to the diaper by said panel.

10. The modified diaper of claim 8 wherein said upper said section of said diaper is adjustably fastened to said panel by replacing said complementary spaced female and male snap fasteners with a strip of complementary hook and loop material affixed over the entire surface of said semicircular intermediate structures.

11. The modified diaper of claim 8 wherein the diaper has an improved aesthetic appearance by stitching a fringe of lace on arcs of said semicircular intermediate structures of said panel and coloring said panels.

* * * * *